United States Patent [19]
Mitsuhashi et al.

[11] Patent Number: 5,545,528
[45] Date of Patent: Aug. 13, 1996

[54] RAPID SCREENING METHOD OF GENE AMPLIFICATION PRODUCTS IN POLYPROPYLENE PLATES

[75] Inventors: Masato Mitsuhashi; Mieko Ogura, both of Irvine, Calif.

[73] Assignee: Hitachi Chemical Research Center, Irvine, Calif.

[21] Appl. No.: 379,077

[22] Filed: Jan. 26, 1995

Related U.S. Application Data

[63] Continuation of Ser. No. 48,980, Apr. 15, 1993, abandoned.
[51] Int. Cl.$^6$ .............................. C12Q 1/68; C12P 19/34
[52] U.S. Cl. ................................................ 435/6; 435/91.2
[58] Field of Search .......................... 435/6, 91.2, 91.21, 435/91.5, 91.52, 91.51; 422/55, 58, 82.08

[56] References Cited

U.S. PATENT DOCUMENTS

| | | | |
|---|---|---|---|
| 3,582,218 | 6/1971 | Anderson | 356/197 |
| 5,112,736 | 5/1992 | Caldwell et al. | 435/6 |
| 5,232,829 | 8/1993 | Longiaru et al. | 435/6 |

OTHER PUBLICATIONS

Higuchi, Russell, et al.; Bio/Technolkogy, vol. 10, Apr. 1992, Research: "Simultaneous Amplification and Detection of Specific DNA Sequences".

Butcher, Ann, et al.; Clinical Immunology Newsletter 73, vol. 12, No. 5, 1992; "Using PCR for Detection for HIV–1 Infection".

Rye, Hays S., et al.; Analytical Biochemistry 208, 144–150 (1993) "Fluorometric Assay Using Dimeric Dyes for Double–and–Single Stranded DNA and RNA with Picogram Sensitivity".

Kwoh, D. Y., et al.; American Biotechnology Laboratory; vol. 8, No. 13, Oct. 1990; "Target Amplification Systems in Nucleic Acid–based Diagnostic Approaches".

Glazer et al., *Nature*, 359, 859–861 (1992).

Shekarchi et al., *J. Clin. Micro.* 21(1), 92–96 (1985).

*Primary Examiner*—W. Gary Jones
*Assistant Examiner*—Kenneth R. Horlick
*Attorney, Agent, or Firm*—Knobbe Martens Olson & Bear

[57] ABSTRACT

The present invention relates to a method for the rapid screening of gene amplification products on commercially available polypropylene microtiter plates. In one aspect of the invention, polypropylene microtiter plates are used for polymerase chain reaction (PCR) and the amount of nucleic acid sequences amplified through the reaction is quantitated in the same plates. In another aspect of the invention, polypropylene plates are used for detection and quantification of nucleic acids.

26 Claims, 9 Drawing Sheets

1 Polypropylene "Nunc"
2 Polypropylene "Coster"
3 Polystyrene "Coster" COOH
4 Polystyrene "Coster" (-)
5 Polystyrene "Coster" $NH_2$
6 Polystyrene "Nunc" $NH_2$
7 Polystyrene "Sumitomo" $NH_2$
8 Polyvinyl chloride "Falcon"

RAPID SCREENING METHOD OF GENE AMPLIFICATION PRODUCTS IN POLYPROPYLENE PLATES

This application is a continuation of application Ser. No. 08/048,980, filed Apr. 15, 1993, abandoned.

BACKGROUND

1. Field of the Invention

The present invention relates to a method for rapidly screening gene amplification products in commercially available polypropylene microtiter plates.

2. Background of the Art

Gene amplification reactions are powerful tools for generating multiple copies of a nucleic acid sequence from a few. A variety of methods are available, such as, polymerase chain reaction (PCR), self-sustained sequence replication (3SR), beta-Q replicase (βQR), first strand synthesis with DNA polymerase, ligation amplification reaction or ligase-based amplification system (LAR/LAS) and reverse transcription.

Polymerase chain reaction (PCR) is a powerful method for amplifying DNA, and is used in a variety of research fields in both basic biosciences and clinical research. Saiki, R. et al. Science, 230:1350–1354 (1985). PCR has been labeled as one of the most promising techniques for the diagnosis and/or analysis of various disease-related genes. Bernstam, V. A. in "Handbook of Gene Level Diagnostics in Clinical Practice", pp. 19–69 (CRC Press, Boca Raton, Fla., 1992). However, manipulating large numbers of test samples simultaneously has presented an important technical obstacle.

Following gene amplification, test samples are typically analyzed to quantify the amount of the nucleic acid produced. Ordinarily, three well known analytical techniques are used: electrophoresis; hybridization blots; or spectrophotometry.

In electrophoresis, agarose or acrylamide gels containing the amplified fragments are run, followed by staining with an intercalating agent such as ethidium bromide. In hybridization blots, such as Southern blots and Dot blots, the samples are analyzed by annealing with specifically labeled probes. Bernstam, V. A. in "Handbook of Gene Level Diagnostics in Clinical Practice", pp. 19–69 (CRC Press, Boca Raton, Fla., 1992). Both of these analytical techniques are time-consuming and cumbersome when large numbers of test samples are generated.

In the third technique, spectrophotometry, the amount of DNA in a sample is determined by measuring the optical density (OD) of the sample at 260 nm. Sambrook, J., Fritsch, E. F. & Maniatis, T. in "Molecular Cloning, A Laboratory Manual" (2d ed): pp. E.5. (Cold Spring Harbor Press, Cold Spring Harbor, N.Y., 1989). Alternatively, the sample can be labeled with a DNA-binding fluorescent dye and the fluorescence of the sample measured at the dye's excitation wavelength. For example, Hoechst 33258 dye has been used with some success. In one example, a sample was labeled with proprietary dyes and read at a wavelength of 345 nm. Mocharla, R., Mocharla, H. & Hodes, M. E. Nucleic Acids Res.:, 15:10589 (1987). However, measurements of polynucleotide concentrations at $OD_{260}$ or the optimal excitation wavelength for Hoechst dye (345 nm) are not very sensitive through polystyrene or polyvinyl chloride materials. It would provide a tremendous advantage to have gene amplification reactions performed in microtiter wells that were more sensitive to spectrophotometric measurements.

There are a variety of commercially available fluorescent dyes, such as, thiazole orange, or dyes from the general groups of benzoxazolium-4-pyridinium, benzothiazolium-4-pyridinium, benzoxazolium-4-quinolinium, and benzothiazolium-4-quinolinium florescent dyes that show good spectrographic sensitivity for the analysis of nucleic acid sequences. These dyes have excitation wavelengths in the low 400 nm range and emission wavelengths in the high 600 nm range when bound to a nucleic acid sequence. Such dyes are available from Molecular Probes, Inc.

A relatively new dye is Yoyo-1, which has shown promising spectrographic sensitivity for detecting nucleic acids. Glazer, A. N., Rye H. S. Nature, 359:859–861 (1992). Yoyo-1 has an excitation wavelength of 485 nm and an emission wavelength of 530 nm.

Conventionally, microtiter plates have been made from heat sensitive polymeric materials, such as polystyrene and polyvinyl carbonate. These plates do not easily tolerate the repeated heat denaturing processes during PCR. Recently, Coster Corporation (Cambridge, Mass.) and Nunc Corporation (Naperville, Ill.) introduced microtiter plates made from polypropylene. Such plates are significantly more heat stable than polystyrene plates.

However, polypropylene is a partially opaque material, i.e., it appears cloudy or not fully transparent. Thus, it is difficult to see samples once they are in the wells.

Currently, some manufactures provide PCR equipment that could be suitable for analysis of microtiter plates (Integrated Separation Systems, Natick, Mass.; MJ Research, Watertown, Mass., Techne, Princeton, N.J., etc.). Therefore, PCR could, in theory, be easily carried out in microtiter plates.

Accordingly, it would be a great advantage if a system was developed for conducting gene amplification reactions in microtiter plates where both the reaction and the analysis could take place in a single plate without the need for transfer of the products.

BRIEF DESCRIPTION OF THE FIGURES

FIG. 1 is a bar graph comparing detectable fluorescence in polystyrene and polypropylene plates. In these experiments, the final DNA (rat genomic DNA) content was 200 ng. Yoyo-1 dye (1:1000 dilution) was dissolved in 40 mM Tris-acetate, pH 8.0 containing 1 mM EDTA, to a final volume was 50 μl. Data are mean from three wells. 1=Polypropylene plate (Nunc); 2=Polypropylene (Coster), 3=Polystyrene (COOH treated, Coster), 4=Polystyrene (Coster), 5=Polystyrene ($NH_2$ treated, Coster), 6=Polystyrene ($NH_2$ treated, Nunc), 7=Polystyrene ($NH_2$ treated, Sumitomo), 8=Polyvinyl carbonate (Falcon). Fluorescence was measured with a CytoFluor™ 2300 at a sensitivity level of 3.0 with excitation and emission wavelengths of 485 nm and 530 nm, respectively.

FIG. 8 is a bar graph demonstrating the detection of positive PCR products by YOYO-1 fluorescence in Nunc polypropylene microtiter plates (Nunc). The PCR products were obtained from the amplification of various concentrations of c-jun cDNA by Taq polymerase for 40 cycles in Nunc® polypropylene microtiter plates with 0.1 microgram each (lane 1–6) of sense and antisense or 0.01 μg each (lane 7–10), in a final volume of 10pl. Five μl of a 1:500 dilution of YOYO-1 in 40 mM Tris acetate, pH 8.0 containing 0.1 mM EDTA and 2 drops of mineral oil were added to each well, and YOYO-1 fluorescence was measured by a CytoFluor™ 2300. After detection, each sample was analyzed by agarose gel electrophoresis stained with ethidium bromide, in order to detect whether the specific PCR band was visible or not.

SUMMARY OF THE INVENTION

We have discovered that it is possible to conduct both the gene amplification and sample analysis in a single commercially available polypropylene microtiter plate. The polypropylene plates are sufficiently durable to accommodate the high temperatures of amplification methods such as PCR. Moreover, analysis and quantification of the PCR products is quickly available by directly reading stained amplification products in the same polypropylene plates that were used for the reactions. The method is equally applicable to all forms of gene amplification.

In one aspect, the present invention provides a method for the rapid screening and analysis of positive gene amplification samples. This method includes the steps of providing a polypropylene reaction vessel having a plurality of wells, such as a microtiter plate, adding a sample containing a nucleic acid having a sequence to be amplified to one or more of the wells, adding reactants for amplification of the sequence to one or more of the wells containing the nucleic acid, amplifying the sequence in the sample, adding a dye to the sample to form a complex with nucleic acid in the well, optically exciting the sample with light in the visible spectrum, detecting and measuring light energy emitted from the dye in the complex in order to determine the presence of amplified nucleic acid sequence in the well. The dye used in this method can selectively and quantitatively complex with the amplified nucleic acid sequence to form a nucleic acid/dye complex. This complex can emit light energy in response to excitation thereof by light in the visible spectrum. The dye has a DNA partition coefficient in a 10% ethanol/water solution of greater than $1 \times 10^7$. Preferably, the dye has an excitation wavelength of between 400 nm and 700 nm and an emission wavelength of between 400 nm and 700 nm. In one preferred embodiment, the excitation wavelength is 485 nm and the emission wavelength is 530 nm. Yoyo-1, Toto-1 and Toto-3 are three especially preferred dyes for use in the method. In a preferred embodiment, the optically exciting step comprises use of a laser. When Toto-3 is used as a dye, a laser that emits light having a wavelength of 633 nm is preferred. The amplifying step can be performed using a number of different techniques, including polymerase chain reaction (PCR), self-sustained sequence replication (3SR), ligation amplification reaction system (LAR/LAS) or beta-Q replicase (βQR). In an especially preferred embodiment, the method includes layering mineral oil over the reactants in the wells prior to the amplification step. Although there is no particular restriction on the volume of the reaction in which the amplification step takes place, the volume of the reactants and sample is preferably between about 5 μl and about 50 μl, still more preferably between about 10 μl and 20 μl. In order to enhance the transmission of fluorescerise, a substance, such as mineral oil can be applied to the exterior of the reaction vessel.

Another aspect of the present invention provides an assay for the detection of a specific nucleic acid sequence in a human subject. This method includes the step of obtaining a tissue sample from the subject. This tissue sample contains nucleic acid. The method continues by loading the nucleic acid into a well of polypropylene microtiter plate having a plurality of wells, and adding reactants to the well. These reactants are for reaction of the nucleic acid in a gene amplification reaction. Thus, the reactants include at least one nucleic acid primer having a sequence selected so as to allow preferential amplification of the specific nucleic acid sequence. A gene amplification reaction is then conducted on the nucleic acid, thereby amplifying the specific nucleic acid sequence if present in the sample. Thereafter, a dye is added to the well to form a conjugate with nucleic acid present in the well. This dye complexes with the nucleic acid sequences amplified and, when optically excited, produces a detectable emission in the visible spectrum. The dye has a DNA partition coefficient in a 10% ethanol/water solution of greater than $1 \times 10^7$. Yoyo-1, Toto-1 and Toto-3 are three preferred dyes. The method includes optically exciting the nucleic acid conjugated with the dye, detecting and measuring the detectable emission from the dye to determine the quantity of the nucleic acid sequence that was amplified in each well, determining a control level of detectable emission from a well in which nucleic acid has not been amplified, and comparing the amount of detectable emission with the amount of detectable emission in the control. An amount of detectable emission greater than in the control indicates the presence of the specific nucleic acid. In some embodiments of this aspect of the invention, the method includes separating the nucleic acid from the tissue sample. The volume of the reactants and sample is preferably between about 5 µl and about 50 µl; however, other volumes can be used. Various gene amplification reactions can be used, including polymerase chain reaction (PCR), self-sustained sequence replication (3SR), ligation amplification reaction system (LAR/LAS) and beta-Q replicase (βQR). The nucleic acid sequence can be a sequence unique to a particular organism, such as one that causes infectious disease in a mammal.

DETAILED DESCRIPTION OF THE PREFERRED EMBODIMENTS

As mentioned above, the present invention relates to our discovery that it is possible to conduct both the gene amplification reaction and fluorescent sample analysis in a single well of a commercially available polypropylene microtiter plate. Gene amplification in the context of this invention is meant to include amplifying any portion of a nucleotide sequence. Polypropylene microtiter plates are sufficiently durable to accommodate the variable high temperatures of amplification methods such as PCR without detrimental effect to the plate, sample, or amplification reaction. As a part of this discovery, we have determined that analysis and quantification of the gene amplification products is unexpectedly advantageous through the partially opaque polypropylene microtiter plates themselves, thereby providing a one reactant vessel method. We have determined that the partially opaque polypropylene microtiter plates are acutally better, due to a higher detectable fluorescent emmision, than previous plates made from other materials such as polystyrene or polyvinyl chloride. As will be appreciated, the present invention thus makes it possible to rapidly react and screen nucleic acid sequences in a single vessel with great accuracy and efficiency.

The invention provides a significant improvement in reading the results of gene amplification experiments. As discussed in the Background of the Invention, a variety of gene amplification reactions are known to those having ordinary skill in the art. These include for example, PCR, 3SR, βQR, and LAR/LAS.

In PCR, in general, multiple copies of nucleic acid sequences corresponding to a starting nucleic acid sequence are produced through stepwise reactions of (i) reacting a single stranded template nucleic acid sequence with one or more primer sequences, deoxyribonucleoside triphosphates, an inducing agent (i.e., a DNA polymerase), to form a dual stranded nucleic acid sequence consisting of the template and complementary strands; (ii) separating the complementary strand from the template, through, for example, heat denaturization or enzymatic cleavage, and (iii) repeating the process to obtain the desired number of copies. See e.g., U.S. Pat. No. 4,683,202. PCR reactants would normally include the oligonucleotide primers and a DNA polymerase, preferably Taq polymerase, in an appropriate buffer.

Heat denaturation is the preferred method of separating DNA strands to obtain the highest amplification yields in the PCR process. Accordingly, reaction vessels must be extremely durable to accommodate both the relatively high temperatures of the denaturing step, and the combined effects of rising and falling temperatures between the steps.

In 3SR, the reaction depends on continuous cycling of the reverse transcription and RNA transcription reactions to replicate an RNA target molecule by means of cDNA intermediates. Pairs of oligonucleotides are used to prime cDNA synthesis. The tails on oligonucleotides indicate that these primers contain the promoter sequence for the T7 RNA polymerase. Synthesis of a double stranded cDNA which serves as a transcription template for T7 RNA polymerase is carried out. Complete cDNA synthesis is dependent on the digestion of the RNA in the intermediate RNA-DNA heteroduplex by RNase H. Transcription competent cDNAs yield antisense or sense RNA copies of the original target. These transcripts are then converted to cDNAs with reverse transcriptase containing double-stranded promoter sequences which can serve as templates for further RNA synthesis. 3SR reactants would therefore normally include oligonucleotides having a T7 RNA polymerase site, RNase H and reverse transcriptase in an appropriate buffer.

Another method of gene amplification is termed ligation amplification reaction or ligase-based amplification system (LAR/LAS). In this method, a double stranded DNA target is thermally denatured in the presence of two sets of complementary oligonucleotides. Each set of oligonucleotides is specific for one DNA strand and is designed to anneal to the target sequence at adjacent sites. After hybridization, the two oligonucleotides are joined by DNA ligase to form the product. The product is then separated from the target sequence by heat denaturation and both the ligation product and the target then serve as substrate for the next cycle of hybridization and ligation. The reactants in this type of amplification would include the four primers and DNA ligase in an appropriate buffer.

In the Beta-Q-Replicase method, RNA is amplified in a manner similar to the transcription-based amplification system (TAS). During βQR the target RNA molecule (or denatured DNA) is hybridized to one primer oligonucleotide that having a 5' recognition site for Qβ replicase between a T7 (or T3 or SP6) RNA polymerase binding site and a target-complementary sequence (TCS). A second primer, having the 3' recognition site for Qβ replicase in addition to the TCS, is then added, followed by reverse transcription to produce cDNA molecules with both the 3' and 5' Qβ replicase sites. T7 RNA polymerase is then added to transcribe the cDNA into RNA copies of the target molecule. Qβ replicase can then be added to use these RNA transcripts as templates for the synthesis of both sense and antisense RNA replication products. The βQR method uses reactants comprising Beta-Q replicase, a primer with the 5' βQR site, a primer with the 3' βQR site, reverse transcriptase, T7 RNA polymerase and the appropriate buffers.

For a review of the aforementioned and other gene amplification methods, see Kwoh et al., *American Biotechnology Laboratory*, 8:14–25 (1990), the disclosure of which is hereby incorporated by reference.

Although PCR is only one of the amplification reactions that can preferably be used in the polypropylene microtiter wells, other gene amplification methods, wherein the end result or products are read by a fluorimeter are also anticipated. For instance, other methods of DNA amplification such as self-sustained sequence replication (3SR), beta-Q replicase (βQR), first strand synthesis with DNA polymerase, reverse transcription, and any other methods known to those of skill in the art are contemplated in accordance with the present invention. These methods are discussed in the background section above, and thoughout references in the analagous art.

In a preferred embodiment of the present invention, a rapid method of screening and analyzing nucleic acids after polymerase chain reaction (PCR) is provided. The method is accomplished in a single polypropylene reaction vessel such as a microtiter plate having multiple wells. Such vessels are commercially available as, for example, 96 well microtiter plates (Coster® Corporation, Cambridge, Mass.) or (Nunc® Corporation, Naperville, Ill.). Coster polypropylene plates have wells with rounded bottoms, and can hold a total volume in each well of approximately 200 μl.

The use of polypropylene reaction vessels is an important feature to the present invention, since such vessels are capable of withstanding the relatively high temperatures under which the PCR techniques are conducted. It will be appreciated, however, that other polymeric materials may exist or may be created possessing similar properties to polypropylene that would also render them suitable for use in the present invention. Such materials are also contemplated for use in connection with the present invention.

In a preferred PCR method, the chosen reaction mixture is added to each well of a microtiter plate. The reaction mixture consists of the typical reagents used in PCR. For example the conventional reactants would be the nucleic acid sequence to be amplified, one or more primers, an inducer, and nucleic acids (dATP, dCTP, dGTP and dTTP) in an appropriate buffer.

Generally, once the reaction mixture has been prepared and loaded in the polypropylene reaction vessel, mineral oil is added to the wells to reduce the evaporation of the reaction solution. Only a few drops (i.e., 10–20 μl) of oil are necessary to prevent evaporation.

In the PCR amplification method, once the reactants are assembled and prepared as above, the reaction vessel is alternately heated and cooled by methods well known in the art, so as to promote amplification of the chosen nucleic acid sequence. For example, amplification in a Nunc microtiter plate can be performed automatically by a cycling system from MJ Research. Other automated machinery exists for cyclically heating incubation vessels such as tubes. The cyclical heating and cooling allows the nucleic acids in the reaction mixture to first extend on the primer complementary to the nucleic acid sequence originally deployed. Thereafter, the complementary strands anneal to form a double stranded molecule. Finally, the strands are denatured at high temperature to form single stranded sequences that can then react to produce additional copies of the nucleic acid sequence or its complement. Further details of the PCR technique can be found in Erlich, "PCR Technology," Stockton Press (1989) and U.S. Pat. No. 4,683,202, the disclosure of which is incorporated herein by reference.

After the desired number of cycles have been run (i.e., when it is expected that a sufficient number of copies of the nucleic acid sequence have been prepared) the reaction vessel is cooled under conditions designed to terminate the reaction, and a fluorescent dye is added. In a preferred embodiment, this step is conducted so as to retain the double-strandedness of any nucleic acid sequence produced. In another preferred embodiment, the dye is one which is capable of quantitatively reacting with all the nucleic acid sequences in the sample and when optically excited will produce a detectable emission in the visible range. It will be appreciated that this step allows the same reaction vessel to be used for quantifying the amount of nucleic acid sequences produced.

It should be understood, however, that the reaction vessel should be capable of efficiently transmitting the wavelengths of optical energy from the light source to excite the stranded nucleic acid molecules and the wavelengths produced after their excitation to the spectrophotometric sensor. Wavelengths of light in the ultra violet range are usually not efficiently transmitted by materials such as polypropylene.

Moreover, until the present invention, it was not expected that polypropylene, due to its cloudy appearance, would be a useful container for spectrophotometry. One would not expect polypropylene to efficiently transmit sufficient visible light to allow detection of stained DNA molecules. However, we have surprisingly discovered that polypropylene plates have less background noise and permit clearer transmission of detectable light, relative to background, than either polystyrene or polyvinyl carbonate. This finding was particularly evident in the photometric range of 450 nm to 700 nm. Table 1 below describes various dyes which could be used in the present invention.

TABLE 1

Characteristics of Molecular Probes'
New Thiazolium and Axazolium Nucleic Acid Stains

| Catalog Number | Dye* | EX max/ EM max (nm)** | $\epsilon \times 10^{-3}$†/ (QY)** | Kp‡ |
| --- | --- | --- | --- | --- |
| None | Thiazole orange | 509/525 | 54/(0.2) | $4.8 \times 10^6$ |
| P-3581 | PO-PRO-1 | 435/455 | 50/(0.39) | $2.0 \times 10^6$ |
| B-3583 | BO-PRO-1 | 462/481 | 58/(0.16) | $3.2 \times 10^6$ |
| Y-3603 | YO-PRO-1 | 491/509 | 52/(0.44) | $8.2 \times 10^6$ |
| T-3602 | TO-PRO-1 | 515/531 | 62/(0.25) | $2.0 \times 10^7$ |
| P-3585 | PO-PRO-3 | 539/567 | nd/(nd) | nd |
| B-3587 | BO-PRO-3 | 575/599 | nd/(nd) | $4.8 \times 10^6$ |
| Y-3607 | YO-PRO-3 | 612/631 | 100/(0.16) | $3.3 \times 10^6$ |
| T-3605 | TO-PRO-3 | 642/661 | 102/(0.11) | $6.2 \times 10^6$ |
| P-3580 | POPO-1 | 434/456 | nd/(nd) | nd |
| B-3582 | BOBO-1 | 462/481 | nd/(nd) | nd |
| Y-3601 | YOYO-L | 491/509 | 84/(0.52) | $6.0 \times 10^8$ |
| T-3600 | TOTO-1 | 514/533 | 112/(0.34) | $1.1 \times 10^9$ |
| P-3584 | POPO-3 | 534/570 | 146/(0.46) | nd |
| B-3586 | BOBO-3 | 570/602 | 148/(0.39) | nd |
| Y-3606 | YOYO-3 | 612/631 | 167/(0.15) | $1.5 \times 10^8$ |

TABLE 1-continued

Characteristics of Molecular Probes'
New Thiazolium and Axazolium Nucleic Acid Stains

| Catalog Number | Dye* | EX max/ EM max (nm)** | $\epsilon \times 10^{-3}$†/ (QY)** | Kp‡ |
|---|---|---|---|---|
| T-3604 | TOTO-3 | 642/660 | 154/(0.06) | $2.5 \times 10^8$ |
| E-1169 | EthD-1 | 528/617 | 7.4/(0.08) | $5.0 \times 10^8$ |
| E-3599 | EthD-2 | 535/626 | nd/(nd) | $1.0 \times 10^9$ |

*All the PO stains are benzoxazolium-4-pyridinium dyes. BO stains are benzothiazolim-4-pyridinium dyes. YO stains are benzoxazolium-4-quinolinium dyes. TO stains are benzothiazolium-4-quinolinium dyes.
**Quantum yields (QY) and spectral data are of the dye bound to excess calf thymus DNA (50 bp/dye).
†$cm^{-1}M^{-1}$
‡DNA partition coefficient in a 10% ethanol/water solution
nd Not determined Table 1 lists various different dyes and their corresponding DNA partition coefficients. These coefficients are related to the amount of dye that remains in a DNA sample after saturation in a 10% ethanol/water solution. A dye having a coefficient of at least $1 \times 10^7$ (i.e. $1 \times 10^7$ times more dye bound to the DNA sample than in the ethanol/water solution) is preferred in this invention as these dyes intercolate with the DNA very efficiently.

One preferred dye is TOTO-3 because it can be excited with a 630 nm laser which is available to those in the art. In addition, TOTO-3 emits photons, upon excitation, at 660 nm, which is different enough from the excitation wavelength to provide easy detection.

Another preferred photometric dye for staining polynucleotides is Yoyo-1, a fluorescent complex that intercalates and reacts with double-stranded nucleic acid sequences. Specifically, Yoyo-1 is an oxazole yellow homodimer.

When complexed with a double-stranded piece of DNA, a multichromophore label is formed that can be subjected to a fluorescence assay. Glazer, A. N. et al. *Nature*, 359:859–861 (1992). Yoyo-1 has an excitation wavelength of 485 nm. After excitation Yoyo-1 emits photons at 530 nm. Both of these wavelengths are in the visible light spectrum.

Other dyes are also contemplated, such as, Toto-1, thiazole orange, or those dyes within the group of benzoxazolium-4-pyridinium, benzothiazolium-4-pyridinium, benzoxazolium-4-quinolinium, and benzothiazolium-4-quinolinium florescent dyes that show advantageous spectrographic sensitivity for the analysis of nucleic acid sequences. These dyes have excitation wavelengths from the low 400 nm range and emission wavelengths up to the high 600 nm range when bound to a nucleic acid sequence. Such dyes are commercially available from companies such as Molecular Probes, Inc.

Even with the cloudy appearance of polypropylene, we have discovered that these plates provide an appropriate analytical chamber for spectrophotometric measurements. Each well is sufficiently transparent to the excitation wavelength and fluorescent emission of the above dyes, such as Yoyo-1, to provide an accurate measurement. In fact, polypropylene provides an even greater transmission of light, relative to background, as the intensity of the emission is increased when compared to clear polyvinyl or polystyrene plates.

Continuing with the preferred method, the samples in the reaction vessel are next optically excited with a wavelength of light that induces photon emissions by the dye so that the quantity of photons can be correlated with amount of nucleic acid in the sample. In this step, it will be understood that when Yoyo-1 is used as the dye, optical excitation can be accomplished at 485 nm, and detection is performed at 530 nm. Moreover, we have discovered that a more linear curve of emission is generated when mineral oil is not removed from the sample prior to analysis. The quantity of mineral on top of the sample was found to be unimportant.

Moreover, in another interesting discovery, the detection of fluorescence through polypropylene plates was enhanced following application of mineral to the outer surface of the microtiter plates. While not wishing to be bound by any particular theory, we believe that this enhancement may be due to reducing the diffusion caused by the opacity of the polypropylene material. We expect that a similar enhancement is possible through the application of any appropriate smoothing substance to the outside of a polypropylene plate. The substance should, however, be sufficiently non-volatile so as not to evaporate too rapidly. Also, it may be possible to polish the outside of the plate, so as to provide a similar effect.

Figure 8:
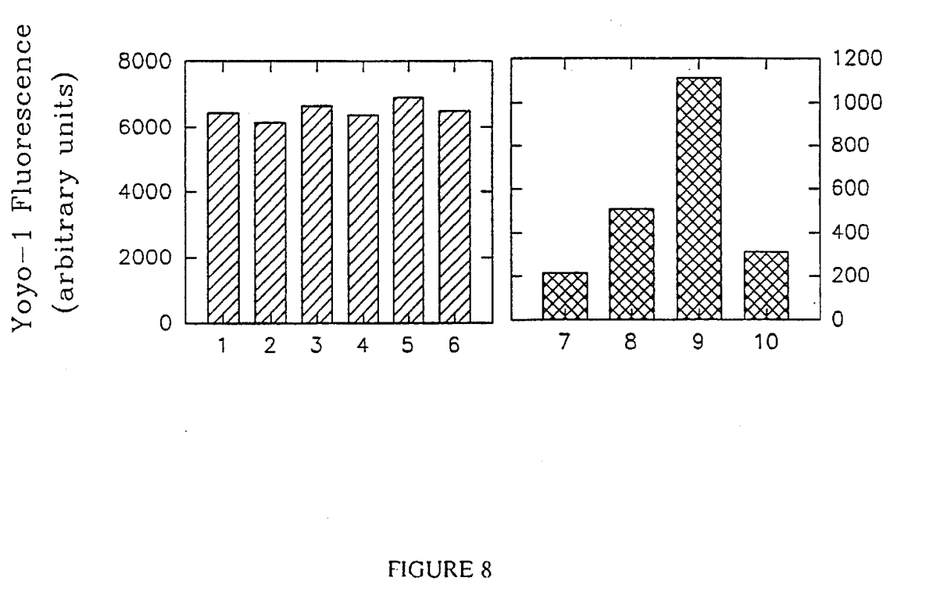
Figure 9:
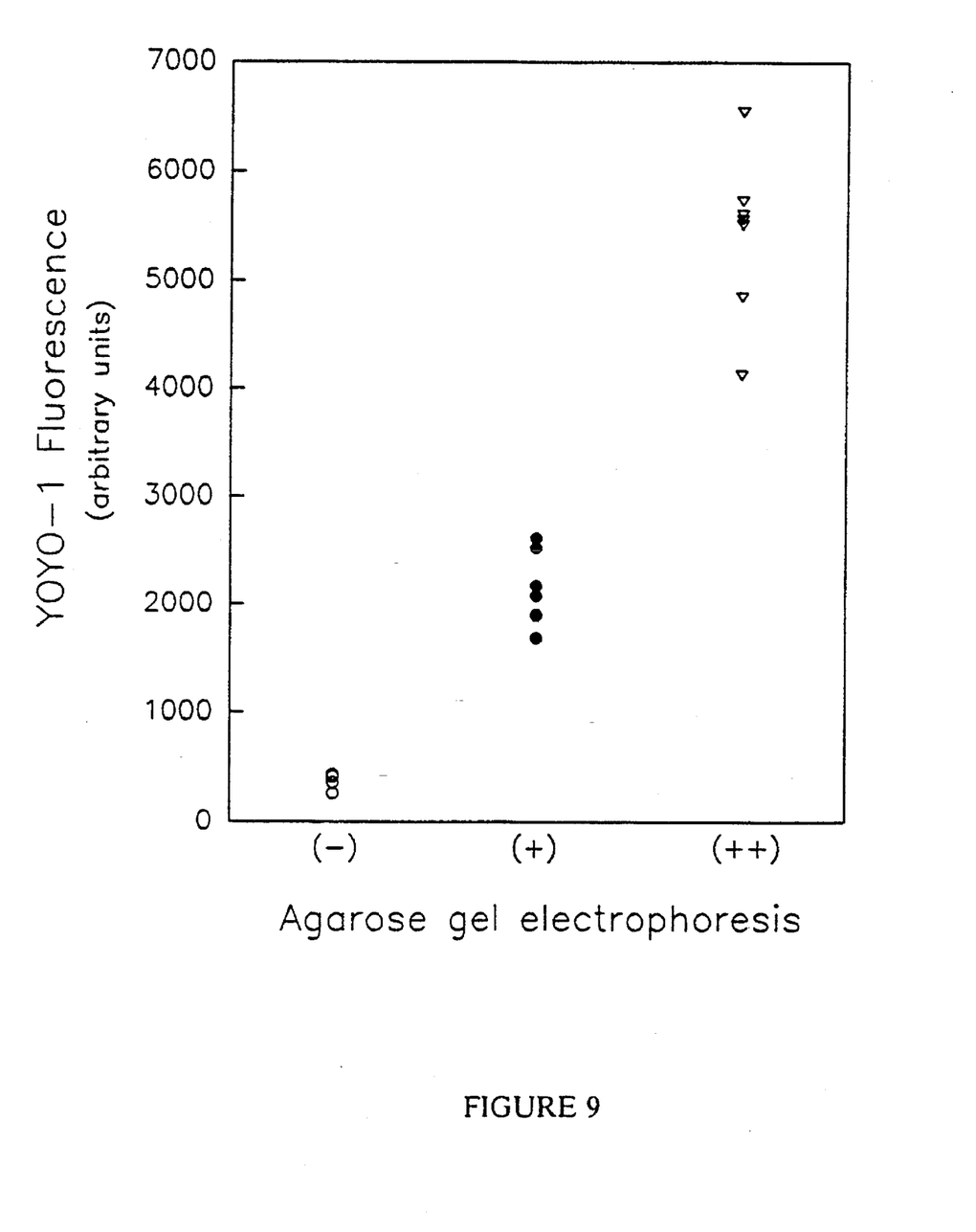
FIG. 9 is a point graph showing the detection of positive PCR products from colon biopsy specimens correlating Yoyo-1 fluorimetry results and agarose gel electrophoresis. cDNA from colon biopsy specimens were obtained. The jun oncogene was then amplified from cDNA by PCR in a Coster polypropylene plate (Coster) through 40 cycles of manual PCR using three water baths. After PCR, 10 μl of a 1:500 dilution of YOYO-1 in 4 mM Tris acetate, pH 8.2 containing 0.1 mM EDTA was added into each well, and YOYO-1 fluorescence was measured by a CytoFluor™ 2300 (y-axis). After Yoyo-1 reading, each sample was analyzed by agarose gel electrophoresis stained with ethidium bromide, in order to detect whether the specific PCR band was visible or not (x-axis).

The method of the present invention requires optimizing primer concentrations in order to obtain higher yields in a PCR procedure. Yoyo-1 is also capable of binding to primers. Thus, high concentrations of primers, as shown in lanes 1–6, can sometimes mask the result of amplified gene products. For example, a battery of primers can be prepared and loaded in individual wells of a microtiter plate with the nucleic acid sequence to be amplified. PCR can be run and the appropriate dye, such as Yoyo-1, can be added to the wells. Thereafter, the plates can be optically excited and their emissions detected with a spectrophotometer. Through the use of standard curve fitting techniques, the quantity of the nucleic acid sequence can be estimated with precision. Only the wells that exceed a threshold amount of nucleic acid in the analysis are then chosen for further analysis, i.e., through gel electrophoresis or blotting techniques, to verify the size and quantity of nucleic acid produced.

Other rapid screening procedures can also be envisioned. For example, a sample of a gene from a patient in which a certain abnormality, such as a defect, addition or other mutation, is believed to exist can be tested through the method of the present invention. It is known that highly specific primer sequences can be prepared allowing the preferential amplification of specific nucleic acid sequences.

Thus, common restriction nucleases can be used to cleave genomic DNA from the patient. The fragments are then placed in polypropylene microtiter plates, and subjected to gene amplification with one or more primers specific for the defective gene. Thereafter, the existence of the defect will be evidenced by DNA amplification in a sample well from the patient when compared to a negative control.

As will be appreciated, in addition to the detection of genetic defects or diseases, the present invention has beneficial use in the detection of infectious diseases, such as, hepatitis, acquired immune deficiency syndrome (AIDS), mycobacterium, methicillin resistant staphylococcus aureus (MRSA), and others.

The other common gene amplification procedures, such as 3SR or βQR, can also be conducted as described above. Further details, objects, and advantages of the present invention will be apparent through a review of the following non-limiting Experiments and the accompanying Figures.

EXPERIMENT 1

Preparation of Oligonucleotide Primers

We prepared oligonucleotide primers for use in the present experiments as follows:

Two oligonucleotide primers were prepared (sense, 5'-CCGCTGTCCCCCATCGACATGG- 3'0 (SEQ ID NO. 1) and antisense 5'-GACAAATTCGACGCGGTGGAC- 3'; (SEQ ID NO. 2) through synthesis in a DNA synthesizer (type 380B, Applied Biosystems, San Jose, Calif.). After ammonium hydroxide treatment at 55° C. overnight, synthesized oligonucleotides were dried, resuspended in water at 0.05 µg/µl, and stored at −20° C. until use. The chemicals for oligonucleotide synthesis were obtained from Applied Biosystems (Foster City, Calif.). Other synthesis reactants chemicals were obtained from Sigma (St. Louis, Mo.).

To obtain nucleic acid sequences to amplify through PCR, we isolated and purified nucleic acid materials from colon biopsy samples.

EXPERIMENT 2

Preparation of cDNA from Colon Bioposy Specimens

Fresh biopsy materials were obtained from patients with colon cancer during operation at University Hospital of Yokohama City Medical School (Yokohama, Japan. The biopsy tissue was quickly frozen in liquid nitrogen until use. As needed, frozen specimens were mixed with equal volume of lysis buffer (10 mM Tris, pH 7.6, 1 mM EDTA, 0.5M NaCl, 0.5% SDS) and buffer-saturated phenol/chloroform/isoamyl alcohol (25:24:1 ), and homogenized by Polytron. After centrifugation, the upper aqueous phase was transferred to a fresh tube, and extracted with chloroform followed by an ethanol precipitation.

Pellets from the ethanol precipitation were suspended in hybridization buffer (10 mM Tris, pH 7.6, 1 mM EDTA, 0.5M NaCl), and 50 µl of test samples were added into each well of plastic microtiter plates (GenePlat™, Hitachi Chemical Research Center, Calif.), in which poly(dT)-containing oligonucleotides were covalently immobilized, as previously described by Mitsuhashi et al. *Nature*, 357:519–520 (1992). See also U.S. patent applications, Ser. Nos. 07/827,208, filed Jan. 29, 1992 abandoned, 07/827,059, filed March 24, 1992, abandoned and 07/974,409, filed November 12, 1992, the disclosures of which are hereby incorporated by reference.

After hybridization of mRNA from the tissue to the immobilized oligo(dT) nucleotides, wells were washed twice with hybridization buffer (10 mM Tris, pH 7.6, 1 mM EDTA, 0.5M NaCl), then 50 µl of RT buffer (50 mM Tris-HCl, pH 8.3, 75 mM KCl, 3 mM $MgCl_2$, 10 mM DTT, 0.5 mM each of dATP, dCTP, dGTP, and dTTP) containing 100 units/well of reverse transcriptase were added into each well to synthesize the first strand cDNA using the hybridized mRNA as a template. Following first strand synthesis, each well was resuspended in 50 pl of cDNA buffer (25 mM Tris-HCl, pH 7.5, 100 mM KCl, 5 mM $MgCl_2$, 10 mM $(NH_4)_2SO_4$, 0.15 mM β-AND+, 250 mM each of dATP, dCTP, dGTP, dTTP, 1.2 mM DTT), containing 0.4 units of RNaseH, 2.5 units of DNA ligase, and 7.5 units of DNA polymerase I. The plates were then incubated at 16° C. overnight to digest the RNA and synthesize the second DNA strand.

After the second strand cDNA synthesis, each well was washed with hybridization buffer 3–5 times, followed by addition of 50 µl of DNase-free water. Plates were incubated at 80° C. for 10 min to denature the double stranded cDNA, then immediately placed on ice. The water phase, containing the single-stranded sense cDNA was used in our next experiment.

EXPERIMENT 3

Polymerase Chain Reaction

To amplify the single-stranded sense cDNA obtained above, we used the polymerase chain reaction. One µl of the single stranded cDNA obtained in Experiment 2 was mixed with 1 µl Of each of the sense and antisense primers from Experiment 1 and combined in 1 µl of 10×PCR buffer (Promega, Madison, Wis.), containing 0.3 µl of 25 mM $MgCl_{2,\ 0.8}$ µl of 10 mM dNTP mix, and 0.2 µl Of Taq polymerase (Promega) in each well of a 96 well microtiter plate. PCR was carried out either polypropylene tubes, or polypropylene plates (Coster, Nunc). For tubes, PCR was carried out in thermal cycles (model 480. Perkin-Elmer Cetus, Norwalk, Conn.). For Nunc plates, PCR was done in thermal cycles CMJ Research). For Coster plates, PCR was performed by manually soaking into 8 different water baths. Water was added to the mixture in each well to obtain a total volume of 10 µl.

Two drops of mineral oil were layered on the top of each well, and PCR was started using a thermal cycler (model 480, Perkin-Elmer Cetus, Norwalk, Conn.). PCR in plastic plates was carried out by manually soaking each plate in three different water baths. After all the reactions, the mixture was heated at 95° C. for 10 minutes. PCR was carried out with the following cycles 40 times: annealing at 55° C. for 1.5 minutes, extension at 72° C. for 4 minutes, and denaturing at 95° C. for 1.5 minutes.

EXPERIMENT 4

Labeling and Quantitating the PCR Products

In our experiment to label and quantitate the PCR products, we used Yoyo-1, from Yoyo-1 iodide (available from Molecular Probes, Inc., Eugene, Oreg.). The Yoyo-1 iodide was suspended in 40 mM Tris-acetate, pH 8.2, containing 1 mM EDTA (TAE buffer).

After the PCR amplification, Yoyo-1 was added to each well of the microtiter plate to a final concentration of 1:1000. Fluorescence was measured in either the CytoFluor™ 2300 Fluorescence Measurement System (Millipore, Bedford, Mass.) or a fluorimeter (F-2000, Hitachi Instrument, Irvine, Calif.) with excitation and emission wavelengths of 485 nm and 530 nm, respectively.

PCR samples were mixed with 1 µl of 10×loading buffer (0.25% bromophenol blue, 0.25% xylenecyanol FF, and 15% Ficoll, Type 400), and electrophoresis was carried out in 1.5% agarose gel containing 5 µg/ml ethidium bromide by standard, well known methods. After electrophoresis, the amplified DNA bands were visualized by an ultraviolet light.

EXPERIMENT 5

Figure 1:
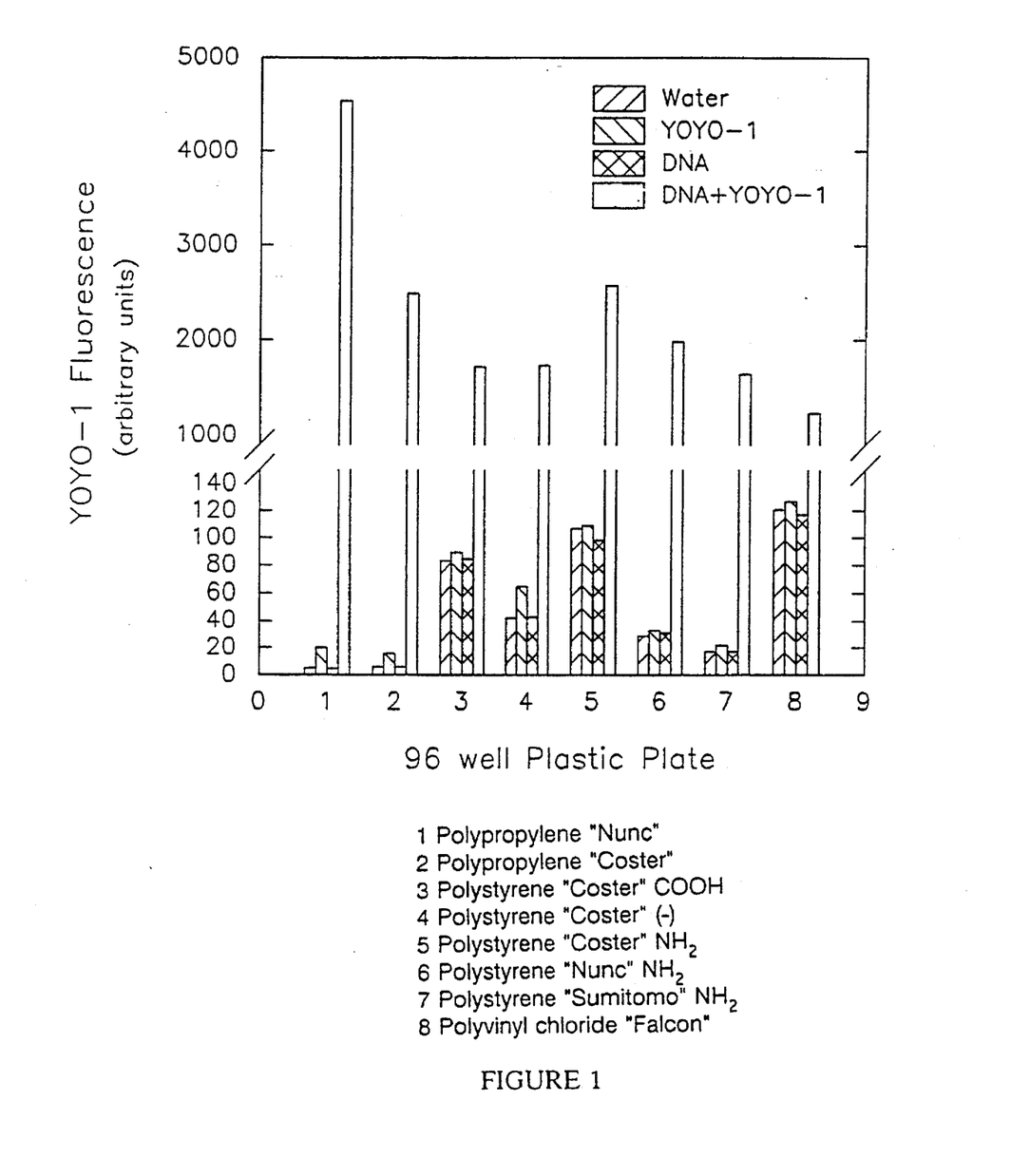

Comparison of the Fluorescence Detectable from Polypropylene Versus Polystyrene Plates Referring now to FIG. 1, we compared the background fluorescence detected from various types of polystyrene, polyvinyl carbonate (Falcon) and polypropylene plates with Yoyo-1 as the fluorescent emitter. To determine background fluorescence, we loaded wells in each plate with either fifty µl of buffer (40 mM Tris-acetate, pH 8.0) 200 ng of rat genomic DNA in 40 mM Tris-acetate (pH 8.0) or Yoyo-1

(1:1000 dilution) in 40 mM Tris-acetate (pH 8.0). For measurements of DNA/Yoyo-1 fluorescence we mixed 200 ng rat genomic DNA with Yoyo-1 (final Yoyo-1 concentration was 1:1000) in Tris-acetate pH 8.0. Fluorescence was then measured by the CytoFluor™ 2300 at a sensitivity level of 3.0, with excitation and emission wavelengths of 485 nm and 530 nm, respectively.

As shown in FIG. 1, where 1=Polypropylene plate (Nunc), 2=Polypropylene (Coster), 3=Polystyrene (COOH treated, Coster), 4=Polystyrene (Coster), 5=Polystyrene ($NH_2$ treated, Coster), 6=Polystyrene ($NH_2$ treated, Nunc), 7=Polystyrene ($NH_2$ treated, Sumitomo), 8=Polyvinyl carbonate (Falcon), the background noise of butter, DNA and Yoyo-1 alone at excitation and emission wavelengths of 485 nm and 530 nm was lower in polypropylene plates than in either polyvinyl carbonate or polystyrene plates. Furthermore, the combined DNA-Yoyo-1 signals on polypropylene plates appeared far more prominent than that those from the polystyrene plates. This experiment demonstrates the advantage of using polypropylene or polyvinyl plates in experiments for detecting DNA fluorescence.

To further analyze the difference among polystyrene, polypropylene and standard quartz glass for their quantitative detection limits of Yoyo-1 fluorescence, various concentrations of DNA were mixed with Yoyo-1, then fluorescence was determined by either the CytoFluor™ or a fluorimeter.

EXPERIMENT 6

Figure 2:
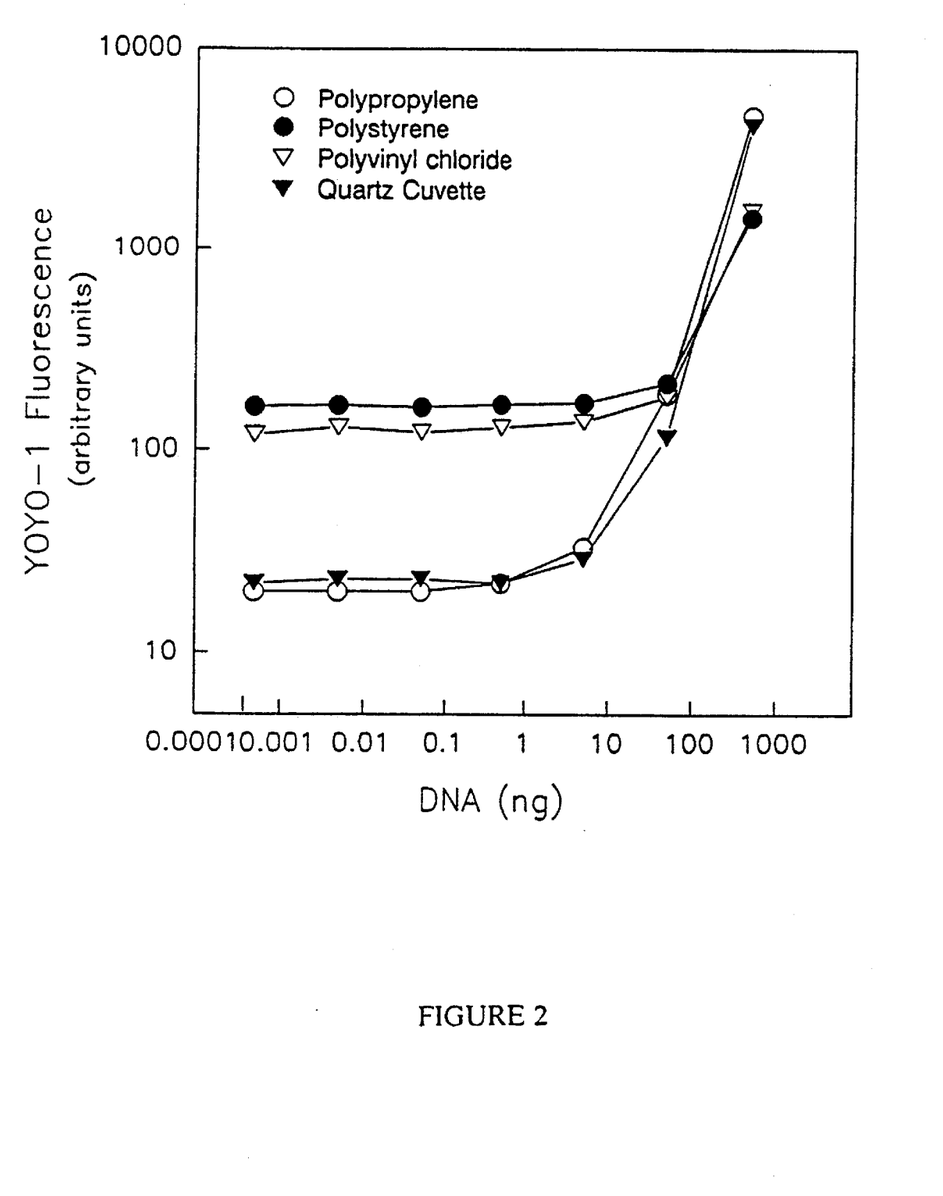
FIG. 2 is a line graph illustrating the dose dependency and detection limit of Yoyo-1 fluorescence as measured from various concentrations of rat genomic DNA mixed with Yoyo-1 at a final Yoyo-1 concentrations of 1:1000 in 50 μl in polystyrene plates (●), polypropylene plates (o), or polyvinyl carbonate (▽) Fluorescence was measured in a CytoFluor™ 2300 at sensitivity levels of 3.0 with excitation and emission wavelengths of 485 nm and 530 nm, respectively. Similar aliquots of DNA-Yoyo-1 mixtures were also loaded in quartz glass cuvettes (▼) and fluorescence was measured in a fluorimeter using similar excitation wavelengths.

Comparison of Quantitative Detection Limits of Polypropylene, Polystyrene, Polyvinyl, and Quartz Referring now to FIG. 2, serially diluted solutions of rat genomic DNA were mixed with Yoyo-1 at a final Yoyo-1 concentration of 1:1000 in a final volume of 50 µl. These samples were loaded into either polystyrene plates (●), polypropylene plates (o), quartz glass cuvettes (▼), or polyvinyl carbonate (▽), Fluorescence was then measured by the CytoFluor™ 2300 at a sensitivity level of 3.0 with excitation and emission wavelengths of 485 nm and 530 nm, respectively. The quartz glass cuvettes were measured in a fluorimeter with similar excitation and emission wavelengths.

It can be seen in FIG. 2 that changes in Yoyo-1 fluorescence on polypropylene plates were detected in the range of 0.25 ng DNA to 12.5 ng DNA with greater clarity than those for either polystyrene or polyvinyl carbonate. The dramatic slope change in the polypropylene plates between concentrations of 12.5 ng and 100 ng further enables more precise measurements of the DNA quantity present in the sample. Further, the strong increase in fluorescence detectable between 0.25 ng and 12.5 ng in the polypropylene, plates as compared to the polystyrene or polyvinyl, would appear to allow the establishment of, for example, threshold DNA values in a sample by setting minimum fluorescence requirements.

We then chose to compare DNA detection efficiencies from various fluorescent dyes.

EXPERIMENT 7

Figure 3:
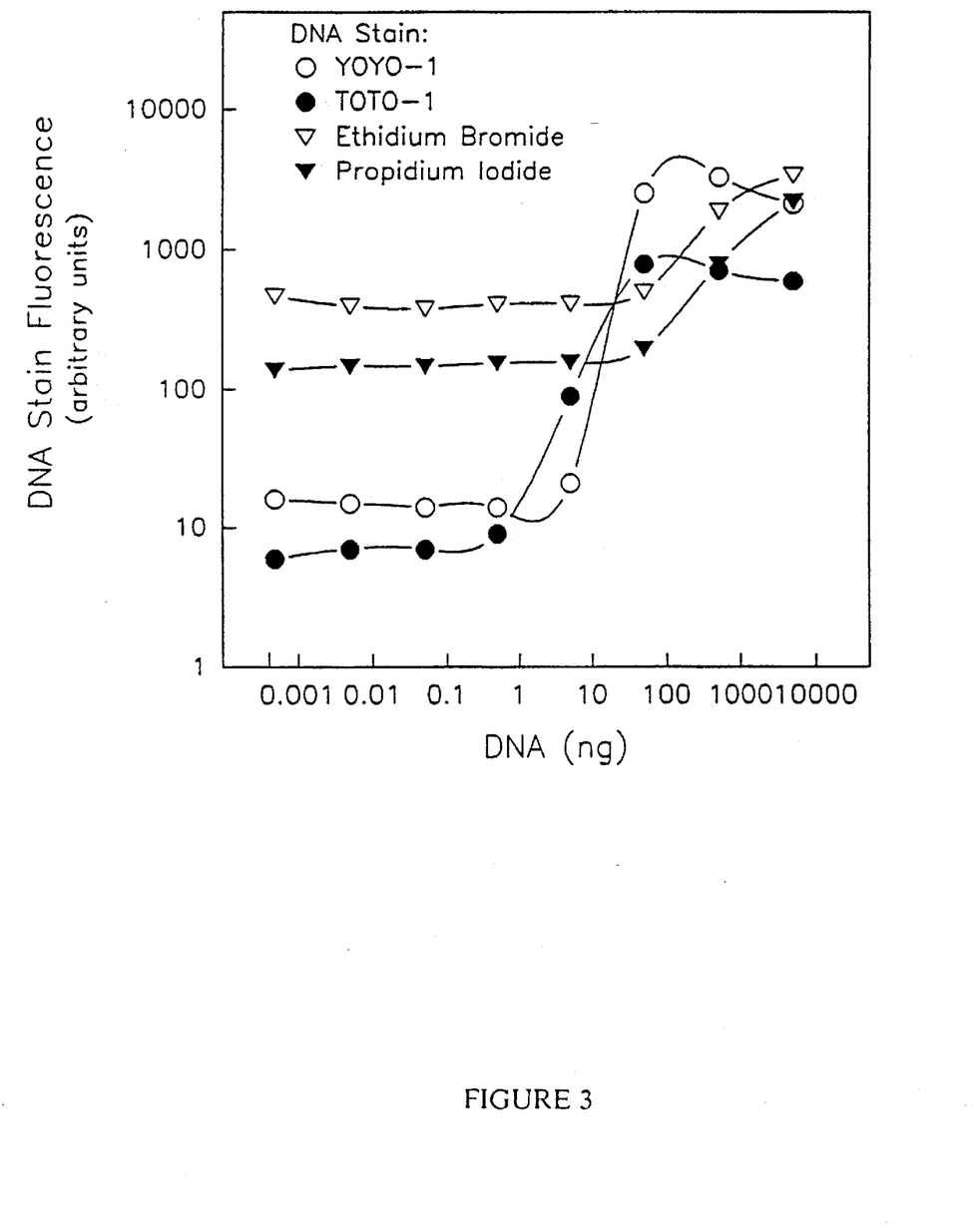
FIG. 3 is a line graph showing a comparison between the detection of Yoyo-1 (o) (final dilution 1:1000), Toto-1 (●) (1:1000), Propidium bromide (▼) (1:100), ethidium iodide (∇) (1:1000), fluorescence at a variety of concentrations of rat genomic DNA in polypropylene plate (Nunc). Fluorescence was measured by the CytoFluor™ 2300 with the following filters: Propidium iodide (excitation, 508/20 nm; emission, 590/35 rim), Ethidium bromide (excitation, 508/20 nm; emission, 590/35 nm), Yoyo-1 (excitation, 485/20 nm; emission, 530/25 nm), and Toto-1 (excitation, 508/20 nm; emission, 560/20 nm).

Comparison of Fluorescence Detection Through Use of a Variety of Fluorescent Dyes In FIG. 3, a comparison of the DNA stain florescence from a variety of chemical dyes is illustrated. The dyes, Yoyo-1 (o) (final dilution 1:1000), Toto-1 (●) (1: 1000), Propidium Iodide (▼) (1:100) and Ethidium Bromide (▽) (7) (1: 1000), were dissolved in 40 mM tris-acetate at a concentration of 1:1000 (except for propidium iodide which was used at a concentration of 1:100). Rat genomic DNA was dissolved to various concentrations (as shown) in 40 mM tris-acetate, pH 8.0, containing 1 mM EDTA in a final volume of 50 µl.

Florescence was then measured on a CytoFluor2300 with appropriate filters to obtain the proper excitation and emission wavelengths, as follows:

| Dye | Excitation | Emission |
| --- | --- | --- |
| Propidium iodide: | 508/20 nm | 590/35 nm |
| Ethidium bromide: | 508/20 nm | 590/35 nm |
| Yoyo-1: | 485/20 nm | 530/25 nm |
| Toto-1: | 508/20 nm | 560/20 nm |

As can be seen, both Yoyo-1 and Toto-1 provide enhanced detection of low concentrations of DNA as compared to either propidium iodide or ethidium bromide. The rapid change in slope illustrated by Yoyo-1 and Toto-1 in the concentration range of 1 ng DNA to 100 ng DNA provides an accurate chart for determining DNA concentrations in these concentrations.

Following our determination of the most advantageous dyes to use in the present invention method, we wanted to determine the effect of small sample volume and mineral oil overlays on the fluorescent detection.

EXPERIMENT 8

Detection of Fluorescence in Sample Sizes Smaller Than 50 µl

Figure 4:
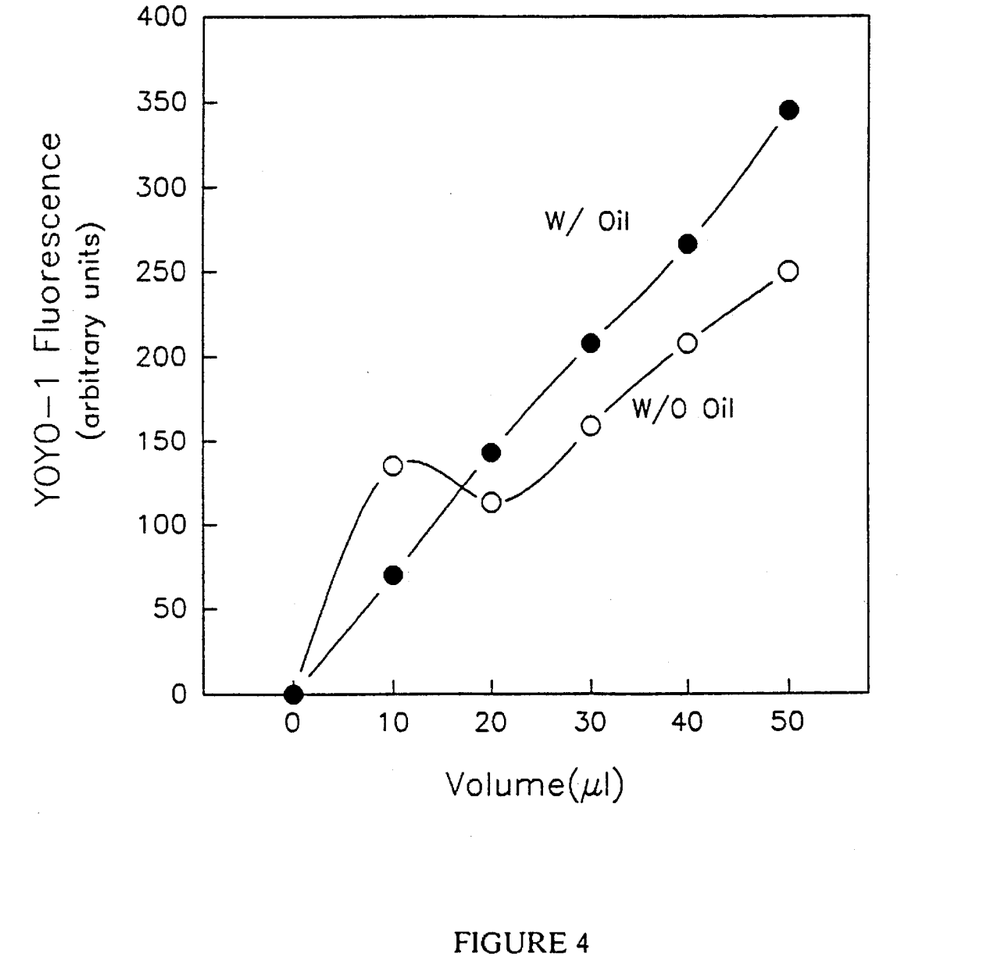
FIG. 4 is a line graph demonstrating the change in Yoyo-1 fluorescence in volumes of less than 50 μl consisting of equal concentrations of calf thymus DNA and 1:500 dilution of Yoyo-1 from which 10–50 μl aliquots were placed into round-bottomed polypropylene microtiter plates (Nunc). Yoyo-1 fluorescence was measured by the CytoFluor™ 2300 at sensitivity levels of 3.0 with excitation and emission wavelengths of 485 nm and 530 nm, respectively. DNA samples were tested with (●) or without (o) one drop of mineral oil.

The minimum volume of liquid that can be housed in a flat-bottomed polystyrene plate is 50 µl. However, less volume can be applied to round-bottomed polypropylene plates, such as those manufactured by Coster and Nunc. FIG. 4 illustrates the change in Yoyo-1 fluorescence in volumes of less than 50 µl consisting of equal quantities of calf thymus DNA and 1:500 dilution of Yoyo-1. Aliquots of between 10–50 µl were placed into round-bottomed polypropylene microtiter plates. Yoyo-1 fluorescence was measured by the CytoFluo™ 2300 at sensitivity levels of 3.0 with excitation and emission wavelengths of 485 nm and 530 nm, respectively, with (●) or without (o) one drop of mineral oil.

In samples without mineral oil overlays where less than 20 µl were applied, we observed that fluorescence detection was not as accurate and did not correlate well with the DNA concentration of the applied volume.

Figure 5:
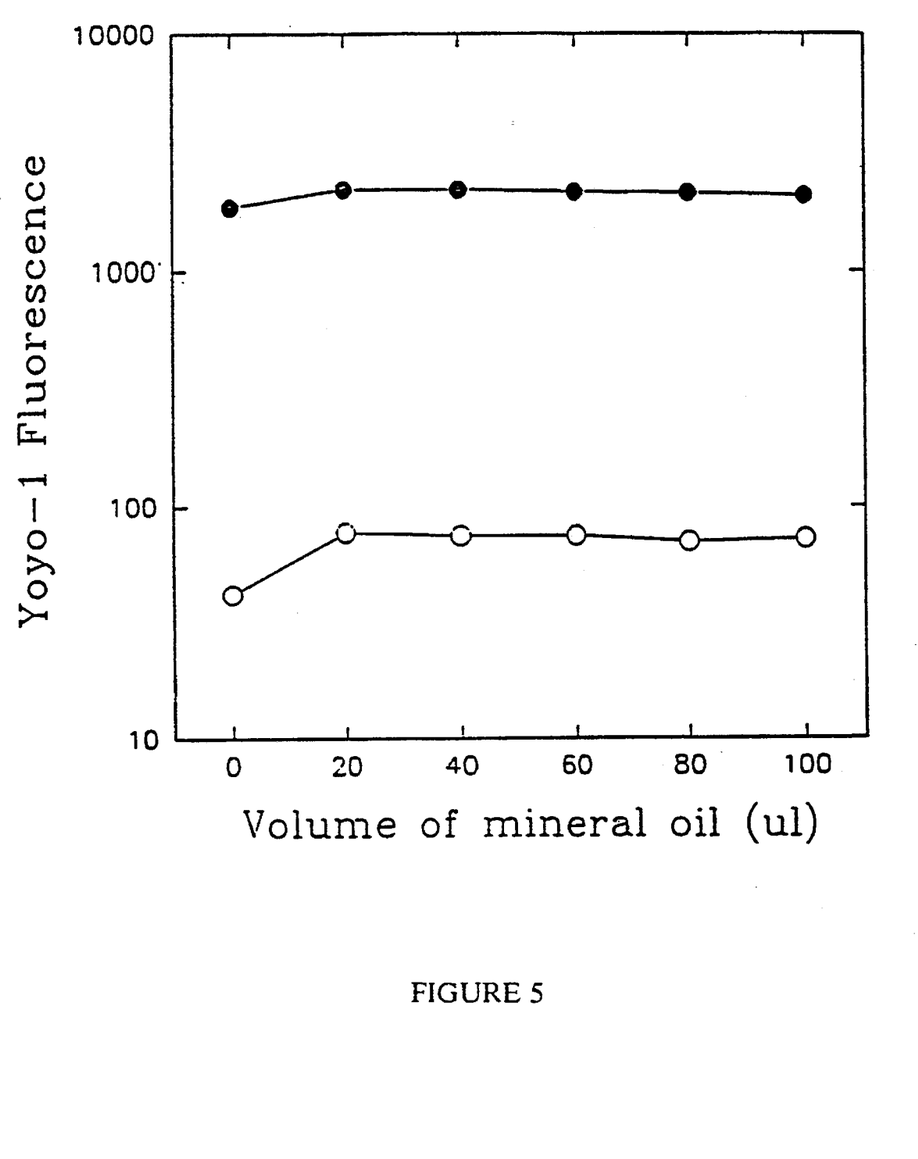
FIG. 5 is a line graph illustrating the effect of mineral oil on Yoyo-1 fluorescence where fifty μl of thymus DNA (●) or buffer (o) and Yoyo-1 (1:1000 dilution) was applied to polypropylene plates. Various volumes of mineral oils were then layered on the surfaces. Yoyo-1 fluorescence was measured by the CytoFluor™ 2300 at sensitivity levels of 3.0 with excitation and emission wavelengths of 485 nm and 530 nm, respectively.

Interestingly, however, if mineral oil was layered onto the surface of the DNA-Yoyo-1 mixture, Yoyo-1 fluorescence was expressed linearly with the applied volume. Further, the amount of mineral oil applied did not affect the level of Yoyo-1 fluorescence. In FIG. 5, the effect of increasing volumes of mineral oil on Yoyo-1 fluorescence is shown. In FIG. 5, fifty µl of buffer (o) or 50 µg (●) thymus DNA and Yoyo-1 (1:1000 dilution) were applied to polypropylene plates, with various volumes of mineral oil (0–100 µl) layered on the surfaces. Yoyo-1 fluorescence was measured by the CytoFluo™ 2300 at sensitivity levels of 3.0 with excitation and emission wavelengths of 485 nm and 530 nm, respectively.

FIG. 5 demonstrates that there is no change in the fluorescence once the mineral oil (20–100 µl) is applied. However, Yoyo-1 fluorescence was slightly increased in the presence of the mineral oil (0–20 μl). Following these experiments with mineral oil in the sample wells decided to test the ability of mineral oil on the outside of the microtiter plates to enhance fluorescent emmisions.

EXPERIMENT 9

Application of Mineral Oil to the Outside of Wells Enhances Fluorescence

Figure 6:
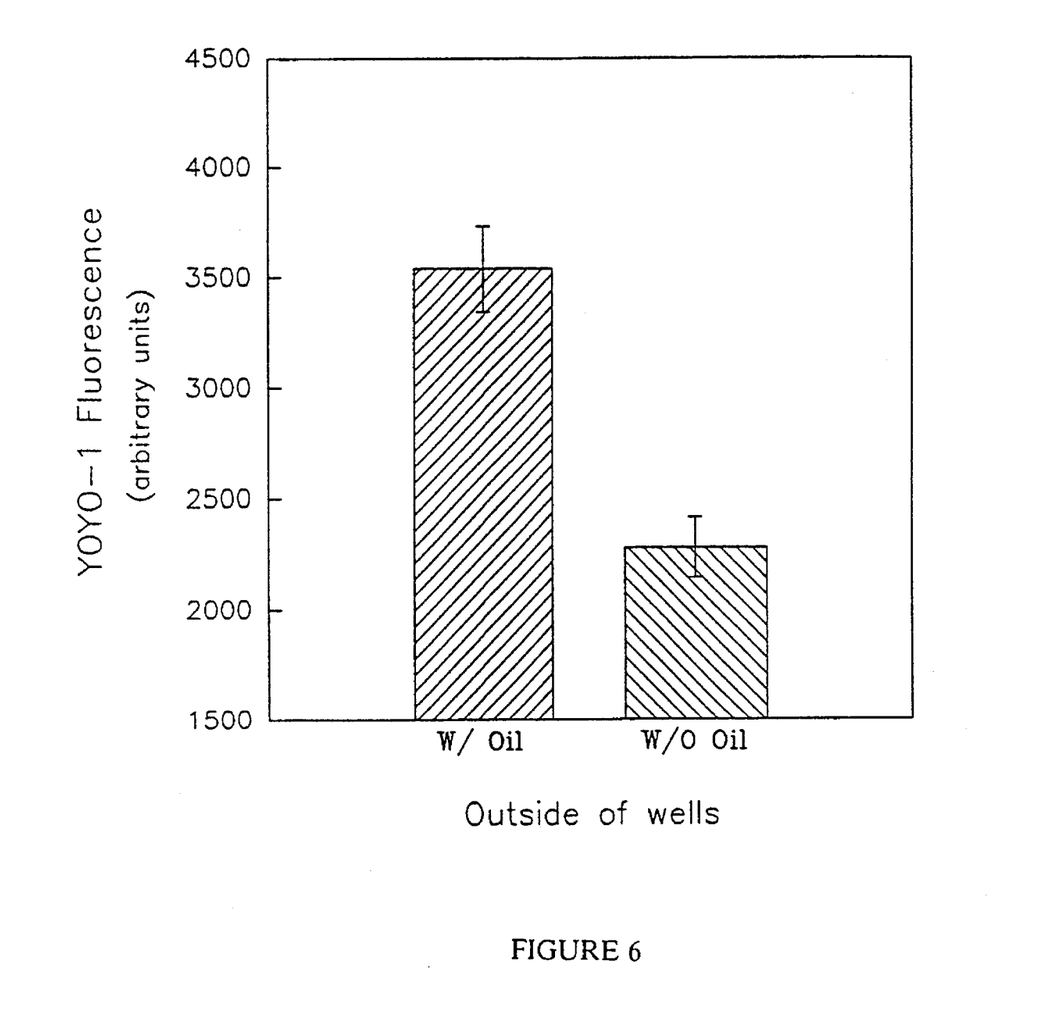
FIG. 6 is a bar graph showing the enhancement of Yoyo-1 fluorescence detection through the application of mineral oil to the outside of polypropylene microtiter plates. The plates were dipped into the mineral oil.

We have also discovered that the detection of fluorescence through polypropylene plates can be enhanced by applying mineral oil to the outside of microtiter wells. Referring now to FIG. 6, rat genomic DNA at 65 ng/well was mixed with Yoyo-1 at a final concentration of 1:1000 in 40 mM Tris-acetate, pH 8.0, containing 1 mM EDTA in a final volume of 50 μl. Plastic wells were then either wetted with mineral or left dry.

The fluorescence observable in the wetted plates was significantly enhanced relative to the non-wetted plates. This provides a heretofore unknown method for enhancing the fluorescent properties of polypropylene microtiter plates.

We also anticipate that other methods that perform the same function as mineral oil can similarly increase the detection of fluorescence in a sample. For example, it is expected that any relatively transparent liquid that does not rapidly evaporate at the detection temperatures will also perform suitably. Additionally, it may be possible to mechanically polish the polypropylene to provide similar features.

EXPERIMENT 10

PCR Amplification of c-JUN DNA and Detection in 10 μl or Less of Solution

We PCR amplified 1 ng of c-jun cDNA (from mouse c-jun clones (American Type Culture Collection, Rockville, Md.)) with Taq polymerase in a thermal cycler as described in Experiment 3. After PCR, the sample was serially diluted (1:2, 1:4, 1:8, 1:16, 1:32, 1:64) with PCR buffer containing dNTP and primers, and 5 μl each of diluted PCR sample was plated into round bottom polypropylene 96 well plates. Five μl of 1:500 dilution of Yoyo-1 in 4 mM Tris acetate, pH 8.2 containing 0.1 mM EDTA and 2 drops of mineral oil were then added into each well, and Yoyo-1 fluorescence was measured by the CytoFluo™ 2300 at sensitivity levels of 3.0 with excitation and emission wavelengths of 485 nm and 530 nm, respectively.

Referring now to FIG. 6, Yoyo-1 fluorescence was quantified through the round bottom polypropylene plates (even with a sample size of 10 μl of PCR solution) under a few drops of mineral oil in a dose dependent manner. Moreover, after Yoyo-1 measurement, PCR samples can be electrophoresed in an agarose gel to confirm the size of the amplified DNA. We have performed this experiment which clearly showed the sensitivity of Yoyo-1 for the detection of positive PCR was similar to that of an agarose gel electrophoresis stained with ethidium bromide.

EXPERIMENT 11

PCR Amplification of c-JUN DNA and Detection in 10 μl or Less of Solution

Since polypropylene plates are the same quality of material as the regular PCR tubes, we PCR amplified various concentrations of c-jun cDNA (from mouse c-jun clones (American Type Culture Collection, Rockville, Md.)) with Taq polymerase in a thermal cycler as described in Experiment 3 except a MJ Research thermal cycler was used, right in Nunc polypropylene microtiter plates. After PCR, Yoyo-1 was added into each well, then Yoyo-1 fluorescence was measured in the CytoFluo™ 2300 at sensitivity levels of 3.0 with excitation and emission wavelengths of 485 nm and 530 nm, respectively. PCR reactions, having DNA, but without added polymerase could be run as a comparison to the amplified sequence.

Figure 7:
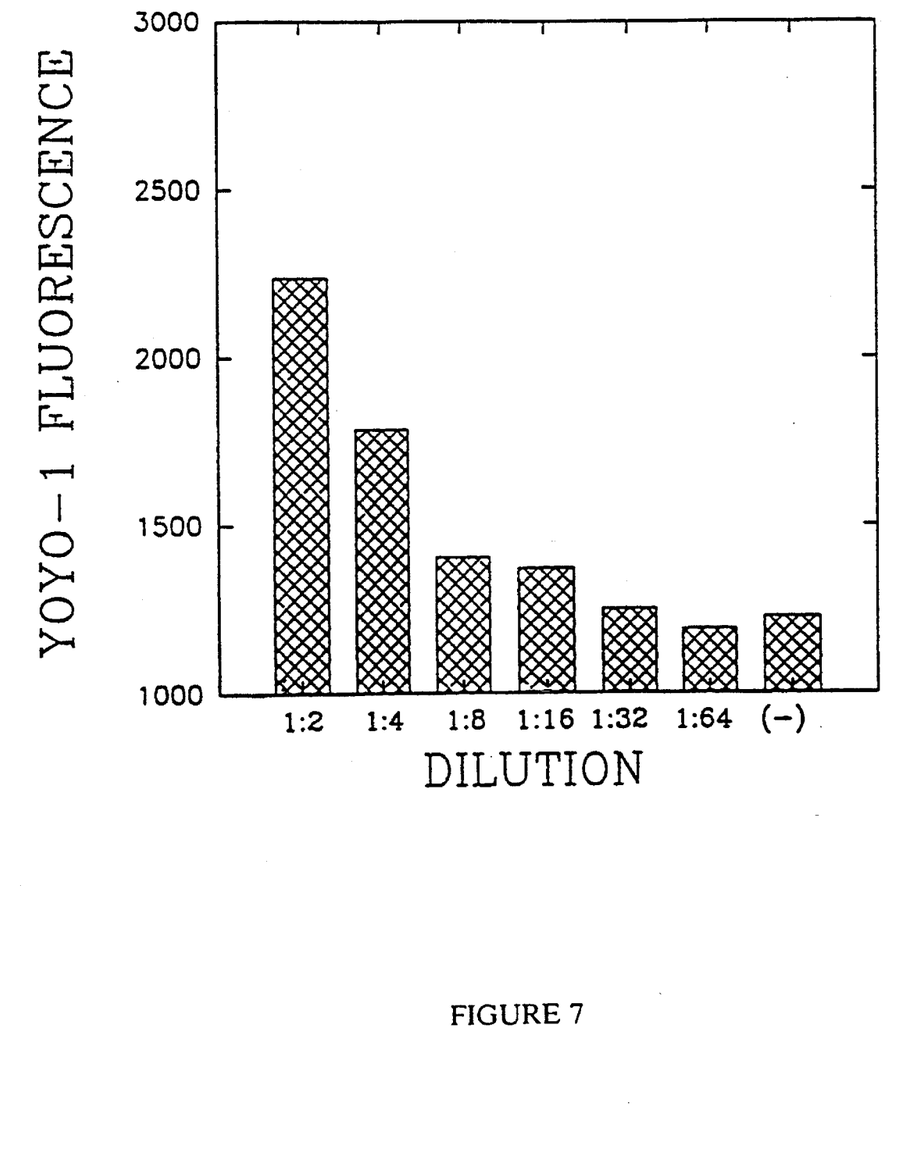
FIG. 7 is a bar graph from an ethidium bromide stained gel demonstrating the detection of positive PCR products by YOYO-1 in Coster polypropylene microtiter plates (Coster). The PCR products were obtained from the amplification of 1 ng of c-jun cDNA by Taq polymerase for 40 cycles in polypropylene tubes. The resulting products were diluted (as shown) with PCR buffer containing dNTP and primers, and 5 μl each of diluted PCR sample was placed into round bottomed polypropylene 96 well microtiter plates (Coster). Five μl of a 1:500 dilution of YOYO-1 in 40 mM Tris acetate, pH 8.2 containing 0.1 mM EDTA and 2 drops of mineral oil were then added into each well, and YOYO-1 fluorescence was measured by a CytoFluor™ 2300. After detection, each sample was analyzed by agarose gel electrophoresis stained with ethidium bromide, in order to detect whether the specific PCR band was visible or not.

Referring now to FIG. 7, detection of Yoyo-1 fluorescence correlated well with the results of agarose gel electrophoresis from clinical specimens.

EXPERIMENT 12

PCR Amplification in NUNC Polypropylene Plates and Detection of Florescence in the Same Plates We conducted PCR with either 0.1 μg of jun sense and antisense primers or with 0.01 μg of each primer from various human cDNA derived from colon biopsy samples. The PCR was carried out as in Experiment 3, however, a thermal cycler from MJ Research that can hold the Nunc® polypropylene plates was used. Thus, after PCR, detection of fluorescence could be accomplished immediately through the addition of Yoyo-1 diluted to a final concentration of 1:500.

In FIG. 8, the results from the above PCR is depicted. The PCR results from 0.1 μg of the jun sense and antisense primers are shown in lanes 1–6 and in lanes 7–10, respectively. The upper half of the Figure shows the results of the same PCR products in agarose gel electrophoresis, stained with ethidium bromide.

Nearly identical detection was possible in a far shorter time through use of the single step amplification and detection of the present invention as compared to electrophoresis. It can be seen, however, that a false positive result was observed where the primer concentration was high in lane 3.

Following our experiments relating to YoYo-1 fluorescence in polypropylene microtiter plates, we performed similar experiments using the dye TOTO-1.

EXPERIMENT 13

DNA Fluorescence with TOTO-3 in Polypropylene Plates (a) We first analyzed TOTO-3 to determine the dye concentration that provided the most advantageous fluorescent readings. Aliquots of a 1 mM TOTO-3 solution (in DMSO) were diluted in 40 mM Tris-acetate, pH 8.0, containing 1 mM EDTA, with each aliquot containing 5 μg/ml or 50 μg/ml of rat genomic DNA. Control dilutions had no DNA. Dilutions of the 1 mM TOTO-3 dye in the range of 1:1000–1:10000 provided the best differential fluorescence between the control and the DNA-containing samples for both concentrations of DNA.

(b) To analyze the time course of TOTO-3 binding to DNA, we added a constant amount of rat genomic DNA to a 1:1000 dilution of TOTO-1, and measured fluorescence. During the first 30 minutes, the amount of DNA added to the diluted TOTO-1 had an almost linear effect on the fluorescence. After 30 minutes, however, increasing time had virtually no effect on the amount of detectable fluorescence.

(c) The above experiments were performed with a Hitachi Fluorescence Spectrophotometer, Model F-2000 at 642nm. We conducted further experiments to determine if fluorescence could be increased by using a laser. For this reason, we chose to study TOTO-3 fluorescence with a 633 nm laser. In this experiment the 633 nm laser produced approximately 5–8 times more fluorescence than excitation by the fluorescence spectrophotometer, even though the spectrophotometer was set for the excitation maximum for TOTO-3.

We have therefore demonstrated the ability to rapidly perform gene amplification in a single polypropylene microtiter well, followed by fluorescent measurements of the amplified products.

It can be appreciated that the present invention should not be limited to the specific embodiments disclosed herein. Rather, the scope of the invention is properly determined upon reference to the following claims.

What we claim is:

1. A method for rapid screening and analysis of positive gene amplification samples, comprising:

providing a polypropylene reaction vessel having a plurality of wells;

adding a sample containing a nucleic acid having a sequence to be amplified to one or more of said wells;

adding reactants for amplification of said sequence to one or more of said wells containing said nucleic acid;

amplifying said sequence in said sample in said well;

adding a dye to the sample in said well, said dye selectively and quantitatively complexing with the amplified nucleic acid sequence to form a nucleic acid/dye complex, said dye in said complex emitting light energy in response to excitation thereof by light in the visible spectrum, said dye having a DNA partition coefficient in a 10% ethanol/water solution of greater than $1\times10^7$;

optically exciting said sample with said light in the visible spectrum;

detecting and measuring light energy emitted from said dye in said complex without transferring said sample from said well in order to determine the presence of amplified nucleic acid sequence in the well.

2. The method of claim 1, wherein the optically exciting step comprises use of a laser.

3. The method of claim 2, wherein the laser emits light having a wavelength of 633 nm.

4. The method of claim 3, wherein said dye is Toto-3.

5. The method of claim 1, wherein the amplifying step is selected from the group consisting of polymerase chain reaction (PCR), self-sustained sequence replication (3SR), ligation amplification reaction system (LAR/LAS) and beta-Q replicase (βQR).

6. The method of claim 1, additionally comprising layering mineral oil over the reactants in the wells prior to the amplification step.

7. The method of claim 1, wherein the reaction vessel is a microtiter plate.

8. The method of claim 1, wherein the dye has an excitation wavelength of between 400 nm and 700 nm and an emission wavelength of between 400 nm and 700 nm.

9. The method of claim 8, wherein the excitation wavelength is 485 nm and the emission wavelength is 530 nm.

10. The method of claim 8, wherein the dye is selected from the group consisting of Yoyo-1, Toto-1 and Toto-3.

11. The method of claim 1, wherein the volume of the reactants and sample is between about 5 μl and about 50 μl.

12. The method of claim 11, wherein the volume of the reactants and sample is between about 10 μl and 20 μl.

13. The method of claim 1, further comprising applying a substance to the exterior of the reaction vessel so as to enhance transmission of the fluorescence.

14. The method of claim 13, wherein said substance comprises mineral oil.

15. An assay for the detection of a specific nucleic acid sequence in a sample containing nucleic acid from a human subject, comprising:

loading said nucleic acid into a well of a polypropylene microtiter plate having a plurality of wells;

adding reactants to said well, said reactants being for reaction of said nucleic acid in a gene amplification reaction, said reactants including at least one nucleic acid primer having a sequence selected so as to allow preferential amplification of said specific nucleic acid sequence;

conducting a gene amplification reaction on the nucleic acid in said well, thereby amplifying said specific nucleic acid sequence if present in said sample;

adding a dye to the well to form a conjugate with nucleic acid present in the well, said dye complexing with the nucleic acid sequence amplified and when optically excited producing a detectable emission in the visible spectrum, said dye having a DNA partition coefficient in a 10% ethanol/water solution of greater than $1 \times 10^7$; and optically exciting the nucleic acid conjugated with the dye;

detecting and measuring the detectable emission from said dye without transferring the sample from said well in order to determine the quantity of the nucleic acid sequence that was amplified in each well;

determining a control level of detectable emission from a well in which nucleic acid has not been amplified; and comparing the amount of detectable emission with the amount of detectable emission in said control, wherein an amount of detectable emission greater than in said control indicates the presence of the specific nucleic acid.

16. The method of claim 15, additionally comprising isolating the nucleic acid from the sample.

17. The method of claim 15, wherein the dye is selected from the group consisting of Yoyo-1, Toto-1 and Toto-3.

18. The method of claim 15, wherein the volume of the reactants and sample is between about 5 μl and about 50 μl.

19. The method of claim 15, wherein the gene amplification reaction is selected from the group consisting of polymerase chain reaction (PCR), self-sustained sequence replication (3SR), ligation amplification reaction system (LAR/LAS) and beta-Q replicase (βQR).

20. The method of claim 15, wherein said nucleic acid sequence comprises a sequence unique to a particular organism.

21. The method of claim 20, wherein said organism is capable of causing infectious disease in a mammal.

22. The assay of claim 15, additionally comprising layering mineral oil over the reactants in the wells prior to conducting the gene amplification reaction.

23. The assay of claim 22, wherein said oil remains layered over the reactants during the detecting step.

24. The method of claim 6, wherein said oil remains layered over the reactants during the detecting step.

25. The method of claim 1, wherein said dye is a thiazolium or azolium dye.

26. The method of claim 15, wherein said dye is a thiazolium or azolium dye.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: NO     ( x i ) SEQUENCE DESCRIPTION: SEQ ID NO:1:

CCGCTGTCCC CCATCGACAT GG      22

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: NO     ( x i ) SEQUENCE DESCRIPTION: SEQ ID NO:2:

GACAAATTCG ACGCGGTGGA C      21